(12) United States Patent
Ukai et al.

(10) Patent No.: US 7,220,762 B1
(45) Date of Patent: May 22, 2007

(54) METHODS FOR STABILIZING BENZIMIDAZOLE COMPOUNDS

(75) Inventors: Koji Ukai, Gifu (JP); Satoshi Fujioka, Ichinomiya (JP); Mitsuru Mizuno, Ichinomiya (JP); Makoto Yokoyama, Ichinomiya (JP); Shigeru Aoki, Gifu (JP); Masao Kawamura, Honjou (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 10/110,679

(22) PCT Filed: Oct. 19, 2000

(86) PCT No.: PCT/JP00/07285

§ 371 (c)(1),
(2), (4) Date: Apr. 16, 2002

(87) PCT Pub. No.: WO01/28559

PCT Pub. Date: Apr. 26, 2001

(30) Foreign Application Priority Data

Oct. 20, 1999 (JP) ................................ 11/298063

(51) Int. Cl.
*A61K 31/4184* (2006.01)
*A61K 31/4439* (2006.01)
*C07D 401/12* (2006.01)

(52) U.S. Cl. .................................... 514/339; 546/273.4
(58) Field of Classification Search ............. 546/273.7, 546/273.4; 514/339; 424/490, 480
See application file for complete search history.

(56) References Cited

U.S. PATENT DOCUMENTS

| | | | |
|---|---|---|---|
| 4,786,505 A | 11/1988 | Lovgren et al. ............. 424/468 |
| 5,039,808 A | 8/1991 | Brändström ................ 546/290 |
| 5,045,321 A | 9/1991 | Makino et al. | |
| 5,093,132 A | 3/1992 | Makino et al. | |
| 5,626,875 A | 5/1997 | Ballester Rodes et al. | |
| 5,690,960 A | 11/1997 | Bengtsson et al. | |
| 5,693,818 A * | 12/1997 | Von Unge ............... 546/273.7 |
| 5,708,017 A | 1/1998 | Dave et al. | |
| 5,817,338 A | 10/1998 | Bergstrand et al. | |
| 5,997,903 A | 12/1999 | Dietrich et al. | |
| 6,030,988 A | 2/2000 | Gilis et al. | |
| 6,090,827 A | 7/2000 | Erickson et al. | |
| 6,248,363 B1 | 6/2001 | Patel et al. | |
| 6,296,876 B1 | 10/2001 | Odidi et al. ................ 424/480 |
| 6,645,988 B2 | 11/2003 | Phillips | |

| | | |
|---|---|---|
| 2002/0039597 A1 | 4/2002 | Ukai et al. |
| 2002/0128293 A1 | 9/2002 | Rampal et al. |
| 2004/0028737 A1 | 2/2004 | Deshpande et al. |
| 2005/0042285 A1 | 2/2005 | Ukai et al. |
| 2005/0244497 A1 | 11/2005 | Sharma |

FOREIGN PATENT DOCUMENTS

| | | | |
|---|---|---|---|
| EP | 0 237 200 A2 | 3/1987 | |
| EP | 0 244 380 B1 | 11/1987 | |
| EP | 0 248 634 A2 | 12/1987 | |
| EP | 0 496 437 B1 | 7/1992 | |
| EP | 0 584 588 A1 | 3/1994 | ............. 546/273.7 |
| EP | 0584588 A1 * | 3/1994 | ............. 546/273.7 |
| EP | 090620 * | 12/1998 | ............. 546/273.7 |
| EP | 0960620 A1 * | 12/1998 | ............. 546/273.7 |
| EP | 0 960 620 A1 | 12/1999 | ............. 546/273.7 |
| GB | 0 189 698 A | 11/1987 | |
| JP | 9-216817 | 2/1987 | |
| JP | 62-277322 | 2/1987 | |
| JP | 62-258320 | 10/1987 | |
| JP | 62-277320 | 11/1987 | ............. 546/273.7 |
| JP | 62-277322 | 12/1987 | ............. 546/273.7 |
| JP | 9-216847 | 8/1997 | |
| JP | 9-511257 | 11/1997 | |
| WO | WO 98/52564 A | 11/1988 | |
| WO | WO 92/22284 | 12/1992 | |
| WO | WO-97/12580 * | 4/1997 | ............. 546/273.7 |
| WO | WO 97/12580 * | 4/1997 | |
| WO | WO 97/25066 A1 | 7/1997 | |
| WO | WO 97/49703 A2 | 12/1997 | |
| WO | WO 98/53798 | 12/1998 | ............. 546/273.7 |
| WO | WO-98/53798 * | 12/1998 | ............. 546/273.7 |
| WO | WO 99/61022 | 12/1999 | |

OTHER PUBLICATIONS

U.S. Appl. No. 10/938,554 filed Sep. 13, 2004.
Tabata et al, "Stabilization of a New Antiulcer Drug (Lansoprazole) in the Solid Dosage Forms," Drug Development and Industrial Pharmacy, 18(13), 1437-1447 (1992); particularly refer to p. 1442; Table 5.

* cited by examiner

*Primary Examiner*—Kamal A. Saeed
*Assistant Examiner*—Janet L Coppins
(74) *Attorney, Agent, or Firm*—Nixon & Vanderhye P.C.

(57) ABSTRACT

The present invention provides a method for stabilizing an oral solid formulation containing a benzimidazole-based compound or a physiologically acceptable salt thereof. That is, it provides a method for stabilizing a benzimidazole-based compound or a physiologically acceptable salt thereof, comprising incorporating 1) a crospovidone or a crospovidone and 2) sodium hydroxide and/or potassium hydroxide to a benzimidazole-based compound or a physiologically acceptable salt thereof.

2 Claims, No Drawings

METHODS FOR STABILIZING BENZIMIDAZOLE COMPOUNDS

TECHNICAL FIELD

The present invention relates to a method for stabilizing a pharmaceutical preparation of the solid dosage form for internal use containing a benzimidazole-based compound or a physiologically acceptable salt thereof.

PRIOR ART

A benzimidazole-based compound or a physiologically acceptable salt thereof has a strong inhibitory action on the so-called proton pump, and it is widely used as a therapeutic agent for stomach ulcer, duodenal ulcer etc., by inhibiting gastric acid secretion. On the other hand, the benzimidazole type compound is chemically very unstable, so various measures have been invented for pharmaceutical manufacturing thereof. For example, JP-A 62-277322 discloses a process for producing a stabilized pharmaceutical composition comprising a basic inorganic salt of magnesium and/or calcium incorporated into a benzimidazole type compound, and JP-A 62-258320 discloses an oral pharmaceutical preparation prepared by incorporating an alkali compound into the portion of a core containing a benzimidazole type compound, then coating it with fillers for tablets soluble in water or rapidly degradable with water or with a polymeric and water-soluble film-forming compound, and further coating it with an enteric coating.

However, the stability of such pharmaceutical preparations is still insufficient even by the prior art described above, so there is demand for further improvements. That is, the object of the invention is to provide a method for further stabilizing a pharmaceutical preparation of the solid dosage form for internal use comprising a benzimidazole-based compound, specifically, a method for preventing it from being colored.

DISCLOSURE OF THE INVENTION

The present invention is a method for stabilizing a benzimidazole-based compound or a physiologically acceptable salt thereof, comprising incorporating a crospovidone to a benzimidazole-based compound represented by the following structure (Formula 1), or a physiologically acceptable salt thereof.

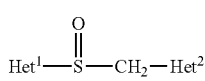

Formula 1

In the formula 1, Het$^1$ is

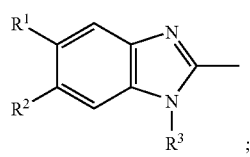

Het$^2$ is

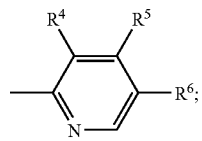

R$^1$ and R$^2$ are the same as or different from each other and are selected from hydrogen, methoxy and difluoromethoxy; R$^3$ is selected from hydrogen and sodium; and R$^4$, R$^5$ and R$^6$ are the same as or different from each other and are selected from hydrogen, methyl, methoxy, methoxypropoxy and trifluoroethoxy.

Furthermore, the present invention is a method for stabilizing a benzimidazole-based compound or a physiologically acceptable salt thereof, comprising incorporating 1) a crospovidone and 2) sodium hydroxide and/or potassium hydroxide to a benzimidazole-based compound represented by Formula 1 or a physiologically acceptable salt thereof.

Furthermore, the present invention is a method for stabilizing a benzimidazole-based compound or a physiologically acceptable salt thereof, comprising coating a core formed by incorporating a crospovidone or 1) crospovidone and 2) sodium hydroxide and/or potassium hydroxide to a benzimidazole-based compound represented by Formula 1 or a physiologically acceptable salt thereof with an enteric coating.

Further, the present invention provides a method for preventing a benzimidazole-based compound or a physiologically acceptable salt thereof from changing in color, which comprises incorporating a crospovidone to the benzimidazole-based compound represented by the above Formula 1 or a physiologically acceptable salt thereof.

In the present invention, a core means a tablet, a granule and the like. A benzimidazole-based compound is extremely unstable in an acidic condition, and once taken orally it is decomposed rapidly upon contact with a gastric acid in a stomach, whereby losing its physiological activity. Accordingly, for the purpose of preventing a decomposition in a stomach, a formulation which is insoluble in the stomach, i.e., a formulation employing an enteric coating over a core containing a benzimidazole-based compound is required.

The present invention is also a method for stabilizing a benzimidazole-based compound or a physiologically acceptable salt thereof, comprising coating a core formed by incorporating a crospovidone or 1) a crospovidone and 2) sodium hydroxide and/or potassium hydroxide to a benzimidazole-based compound represented by Formula (I) or a physiologically acceptable salt thereof with an intermediate coating; and then coating it further with an enteric coating.

An enteric coating is generally an acidic substance, whose direct contact with a benzimidazole-based compound is desired to be avoided. Accordingly, an inactive intermediate film may be provided between a core containing a benzimidazole-based compound and an enteric coating. The term "inactive" used herein means no adverse effect on the stability of a benzimidazole-based compound.

A material for such inactive intermediate film may for example be a water-soluble polymer, water-soluble or water-dispersible material or a water-insoluble material including a crospovidone, hydroxypropyl cellulose, hydroxypropylmethyl cellulose, lactose, mannitol, starch, crystalline cellulose, ethyl cellulose and the like. When an intermediate film is provided using a water-insoluble material as disclosed in JP-A 1-290628, a microparticle of the water-insoluble material may be mixed with the film.

The composition of an intermediate film according to the present invention particularly preferably contains a crospovidone or 1) a crospovidone and 2) hydroxypropyl cellulose and/or ethyl cellulose. In an intermediate film containing 1) a crospovidone and 2) hydroxypropyl cellulose and/or ethyl cellulose, the ratio of the hydroxypropyl cellulose and/or ethyl cellulose is preferably 0.1 to 1 part by weight based on 1 part of a crospovidone.

A benzimidazole-based compound of the present invention or a physiologically acceptable salt may preferably be rabeprazole, omeprazole, pantoprazole, lansoprazole or their salts with sodium, potassium, magnesium and the like. A particularly excellent effect of the present invention is exerted when a benzimidazole-based compound represented by Formula 1 or a physiologically acceptable salt thereof is rabeprazole or its sodium salt.

The structure of each compound is shown in Formula 3.

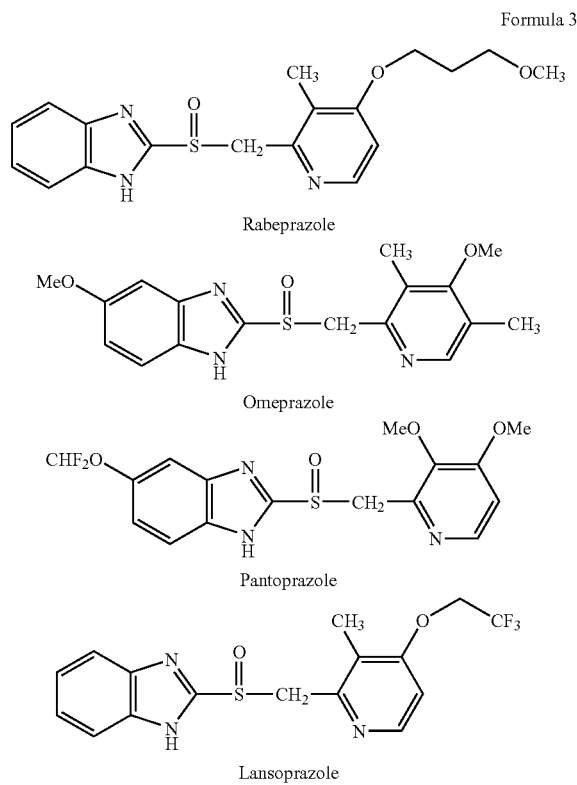

Formula 3

Rabeprazole

Omeprazole

Pantoprazole

Lansoprazole

A benzimidazole-based compound or its physiologically acceptable salt is hereinafter referred to together as a benzimidazole-based compound.

A benzimidazole-based compound of the present invention can be prepared by a method known. For example, it can be prepared by a method disclosed in any of JP-A 52-62275, JP-A 54-141783 and JP-A 1-6270 may be employed.

The weight ratio of a crospovidone to a benzimidazole-based compound in the invention is preferably 0.5 to 5 parts by weight to 1 part of the benzimidazole-based compound.

While it is essential for a composition and/or a formulation containing a benzimidazole-based compound in the present invention to contain a crospovidone. Further, sodium hydroxide, potassium hydroxide and sodium carbonate may also be incorporated each alone or in combination with each other.

The weight ratio of any of sodium hydroxide, potassium hydroxide and sodium carbonate to a benzimidazole-based compound is preferably 0.01 to 2 parts by weight to 1 part of the benzimidazole-based compound.

A benzimidazole-based compound in a composition and/or a formulation supplemented with ordinary additives is extremely unstable and susceptible to a decomposition under a heated and humid storage condition. Such decomposition is accompanied not only with an increase in the impurity levels but also with the change in color of the composition and/or a formulation especially when a benzimidazole-based compound is incorporated.

The present invention is a method for preventing the change in color of a benzimidazole-based compound or its physiologically acceptable salt in a composition and/or a formulation formed by incorporating a crospovidone or 1) crospovidone and 2) sodium hydroxide and/or potassium hydroxide to the benzimidazole-based compound. A term "formulation" used herein means a formulation obtained by coating a core formed by incorporating a crospovidone or 1) a crospovidone and 2) sodium hydroxide and/or potassium hydroxide to a benzimidazole-based compound with an enteric coating or with an intermediate coating which is subsequently coated further with an enteric coating.

A method for stabilizing a benzimidazole-based compound according to the invention is a method exerting an extremely remarkable effect not only in ensuring the constant content of a benzimidazole-based compound and in reducing the amounts of impurities produced but also in suppressing any change in color.

In preparing a formulation using a composition obtained by incorporating a crospovidone or 1) a crospovidone and 2) sodium hydroxide and/or potassium hydroxide to a benzimidazole-based compound according to the present invention, ordinarily employed excipients such as lactose and mannitol may be employed. It is preferred to use hydroxypropyl cellulose as a binder and a crospovidone as a disintegrant.

A crospovidone employed usually as a disintegrant is known to undergo, when being divided finely, a reduction in the disintegrating or swelling ability it possessed naturally. Crospovidone having a small particle diameter after being divided finely and/or sieved is used in the present invention as a stabilizer for a benzimidazole-based compound, and can be used in an amount exceeding the amount when added just as an ordinary disintegrant (10% or less). The average particle diameter of a finely-divided and/or sieved crospovidone is preferably several μm to 50 μm.

Accordingly, in a composition or a formulation according to the present invention, it is preferred to use as a crospovidone a finely-divided crospovidone having an average particle diameter of several μm to 50 μm. It is a matter of course that a finely-divided crospovidone or an ordinary crospovidone are employed in combination.

A composition or a formulation according to the present invention can be produced by a method employed usually.

Thus, a benzimidazole-based compound is incorporated with a crospovidone or 1) a crospovidone and 2) sodium hydroxide and/or potassium hydroxide, and then combined with an excipient and then subjected to a dry or wet granulation and then compressed into a tablet optionally with an added disintegrant such as a crospovidone. It is needless to say that it is not limited to this procedure.

Typically, 10 g of sodium rabeprazole which is a benzimidazole-based compound, 20 g of a crospovidone, 42.7 g of mannitol and 1.5 g of hydroxypropyl cellulose were mixed and then sodium hydroxide and/or potassium hydroxide dissolved or dispersed in ethanol was added in portions to effect a granulation, followed by drying and sieving with a speed mill (16 mesh size). The mixture is combined with 0.8 g of magnesium stearate and then compacted into a 75 mg tablet containing 10 mg of rabeprazole sodium.

Onto the tablet thus obtained, an ethanol solution of hydroxypropyl cellulose in which a crospovidone is dispersed was sprayed using a fluidized bed or a pan coater to form an intermediate film, onto which an ethanol solution or a hydrated ethanol solution of hydroxypropylmethyl cellulose phthalate or an enteric methacrylic acid copolymer to form an enteric coated tablet having an intermediate film.

According to the present invention, a method for stabilizing a benzimidazole-based compound which is extremely unstable can be provided. Effect of the present invention will be described.

Experiments

Effect of Crospovidone in Tablet

The tablets having various crospovidone contents obtained in Examples 1 to 3 described below were stored for one week in a cold place and also at 40° C. and 75% relative humidity (with being opened).

At the same time, a tablet containing no crospovidone was stored as a control for one week as Comparative Example 2.

Each formulation thus stored was evaluated based on the color difference ($\Delta E$), measured by a color difference meter (Model SE-200, NIPPON DENSHOKU KOGYO), as an index of the change in the color coordinate (value (L), hue (a), chroma (b)) observed when stored at 40° C. and 75% relative humidity (with being opened) when compared with the control which was stored in the cold place. A larger color difference ($\Delta E$) reflects a larger coloring of a sample stored at 40° C. and 75% relative humidity when compared with a control stored in the cold place. The values of the color difference ($\Delta E$) of each Example are shown in Table 1.

TABLE 1

| Formulation | Control Example 1 | Example 1 | Example 2 | Example 3 |
|---|---|---|---|---|
| sodium rabeprazole | 20.0 | 20.0 | 20.0 | 20.0 |
| mannitol | 125.4 | 105.4 | 85.4 | 65.4 |
| crospovidone | — | 20.0 | 40.0 | 60.0 |
| sodium hydroxide | 3.0 | 3.0 | 3.0 | 3.0 |
| magnesium stearate | 1.6 | 1.6 | 1.6 | 1.6 |
| (subtotal) preparation property | 150.0 | 150.0 | 150.0 | 150.0 |
| color difference ($\Delta E$) | 40.93 | 23.75 | 16.18 | 14.38 |

Unit:mg

Since the color difference ($\Delta E$) of a sample stored at 40° C. and 75% relative humidity (with being opened) and the change in color of the formulation were both reduced in response to the increase in the amount of the crospovidone added, it became evident that, in the present invention, the crospovidone had an inhibitory effect on the change in color of a benzimidazole-based compound or its physiologically acceptable salt.

Effect of Sodium Hydroxide in Tablet

The tablets having various sodium hydroxide contents obtained in Examples 2 and 4 to 5 described below were stored for one week in a cold place and also at 40° C. and 75% relative humidity (with being opened). At the same time, a tablet containing sodium carbonate was stored as a control 2 for one week.

Each formulation thus stored was evaluated in the manner similar to that described above based on the color difference ($\Delta E$) of a sample stored at 40° C. and 75% relative humidity (with being opened) when compared with the control which was stored in the cold place. A disintegration test of samples stored in a cold place and at 40° C. and 75% relative humidity (with being opened) was also performed according to Japanese Pharmacopoeia. In addition, a high performance liquid chromatography was employed to determine the level (%) of impurities derived from the decomposition of rabeprazole in a tablet stored at 40° C. and 75% relative humidity (with being opened). The results are shown in Table 2.

TABLE 2

| Formulation | Example 2 | Example 4 | Example 5 | Control Example 2 |
|---|---|---|---|---|
| sodium rabeprazole | 20.0 | 20.0 | 20.0 | 20.0 |
| mannitol | 85.4 | 84.8 | 84.4 | 75.4 |
| crospovidone | 40.0 | 40.0 | 40.0 | 40.0 |
| sodium hydroxide | — | 0.6 | 1.0 | — |
| anhydrous sodium carbonate | — | — | — | 10.0 |
| hydroxypropyl cellulose | 3.0 | 3.0 | 3.0 | 3.0 |
| magnesium stearate | 1.6 | 1.6 | 1.6 | 1.6 |
| (subtotal) preparation property | 150.0 | 150.0 | 150.0 | 150.0 |
| color difference ($\Delta E$) | 16.18 | 17.45 | 17.88 | 17.27 |
| disintegration time (min) stored in a cold place | 5.8~6.2 | 3.6~4.1 | 3.7~4.0 | 7.3~8.1 |
| stored at 40° C. and 75% relative humidity (with being opened) | 8.1~10.1 | 4.0~5.1 | 5.5~6.1 | 22.8~24.0 |
| HPLC-measured impurities (%) stored at 40° C. and 75% relative humidity (with being opened) | 2.99 | 2.38 | 2.31 | 1.96 |

Unit:mg

While the color difference ($\Delta E$) of a crospovidone-supplemented sample stored at 40° C. and 75% relative humidity (with being opened) exhibited no substantial change in response to the change in the amount of sodium hydroxide added, the level (%) of the HPLC-measured impurities in a sample stored at 40° C. and 75% relative humidity (with being opened) was reduced in response to the increase in the amount of sodium hydroxide added. Therefore, in the present invention, it is evident that sodium hydroxide has an effectiveness in stabilizing a benzimidazole-based compound or its physiologically acceptable salt.

The addition of sodium carbonate also exhibited a stabilizing effect on the color difference ($\Delta E$) and the HPLC-measured impurity level (%) of a sample stored at 40° C. and 75% relative humidity (with being opened).

On the other hand, the disintegration time of a sodium hydroxide-supplemented sample stored at 40° C. and 75% relative humidity (with being opened) exhibited no change when compared with a sample stored in a cold place, while a sodium carbonate-supplemented sample exhibited a substantially prolonged disintegration time.

It was evident that the stabilizing effect of an additive added together with a crospovidone was higher in a sodium hydroxide-supplemented formulation than in a sodium carbonate-supplemented formulation.

EXAMPLE

The present invention is described in more detail by referring to the following Examples, which are not intended to restrict the invention.

Examples 1 to 3

1 Part by weight of a benzimidazole-based compound was combined with 1 part by weight (Example 1), 2 parts by weight (Example 2) or 3 parts by weight (Example 3) of a crospovidone to formulate a tablet.

Thus, 20 g of rabeprazole sodium was admixed with 20 to 60 g of a crospovidone, 65.4 to 105.4 g of mannitol and 3 g of hydroxypropyl cellulose and then ethanol was added portionwise to effect a wet granulation with stirring. The granule was dried and grained, and then 1.6 g of magnesium stearate was dusted in, and the mixture was then compacted into tablets each of which weighed 150 mg and contained 20 mg of rabeprazole sodium. Each formulation is shown in Table 1.

Examples 4 to 5

1 part by weight of a benzimidazole-based compound was combined with 0.03 parts by weight (Example 4) or 0.05 parts by weight (Example 5) of sodium hydroxide to formulate a tablet.

Thus, 20 g of rabeprazole sodium was admixed with 0.6 to 1.0 g of sodium hydroxide, 40 g of a crospovidone, 84.4 to 84.8 g of mannitol and 3 g of hydroxypropyl cellulose and then 0.6 to 1.0 g of sodium hydroxide dissolved in ethanol was added portionwise to effect a wet granulation with stirring. The granule was dried and grained, and then 1.6 g of magnesium stearate was dusted in, and the mixture was then compacted into tablets each of which weighed 150 mg and contained 20 mg of rabeprazole sodium. Each formulation is shown in Table 2.

Example 6

A tablet obtained in Example 5 was coated with an ethanol solution containing a crospovidone and hydroxypropyl cellulose using a fluidized bet granulator to obtain a tablet having 15 mg of an intermediate film. Subsequently, onto the intermediate film-coated tablet, a hydrated ethanol solution containing hydroxypropyl methylcellulose phthalate, monoglyceride, talc, titanium oxide, iron oxide red and magnesium stearate was sprayed using a fluidized bed granulator, whereby yielding tablets each of which was coated with 15 mg of an enteric coating, weighed 180 mg and contained 20 mg of rabeprazole sodium.

A tablet obtained in Example 6 was packed in a PTP package (bottom sealed with aluminum foil) and stored in a cold place and at 40° C. and 75% relative humidity (with being opened) for one week, and no difference in the HPLC-measured impurity level was noted between the two storage conditions, indicating a stability.

Example 7

A half amount of the formulation of Example 5 was compacted into tablets each of which weighed 75 mg and contained 10 mg of rabeprazole sodium. Onto this tablet, an ethanol solution containing a crospovidone and hydroxypropyl cellulose was coated using a pan coater to obtain a tablet covered with 10 mg of an intermediate film. Onto this intermediate film-coated tablet, a hydrated ethanol solution containing hydroxypropyl methylcellupose phthalate, monoglyceride, talc, titanium oxide, iron oxide yellow and magnesium stearate was sprayed using a pan coater, whereby yielding tablets each of which was coated with 10 mg of an enteric coating, contained 10 mg of rabeprazole sodium and weighed 95 mg.

A tablet obtained in Example 7 was packed in a PTP package and stored in a cold place and at 40° C. and 75% relative humidity (with being opened) for one week, and no difference in the HPLC-measured impurity level was noted between the two storage conditions, indicating a stability.

Example 8

A half amount of the formulation of Example 5 was compacted into tablets each of which weighed 75 mg and contained 10 mg of rabeprazole sodium. Onto this tablet, an ethanol solution containing a crospovidone and ethyl cellulose was coated using a fluidized bed granulator to obtain a tablet covered with 3 mg of an intermediate film. Onto this intermediate film-coated tablet, a hydrated ethanol solution containing hydroxypropyl methylcellulose phthalate, monoglyceride, talc, titanium oxide and magnesium stearate was sprayed using a fluidized bed granulator, whereby yielding tablets each of which was coated with 10 mg of an enteric coating, contained 10 mg of rabeprazole sodium and weighed 90 mg.

A tablet obtained in Example 8 was packed in a PTP package and stored in a cold place and at 40° C. and 75% relative humidity (with being opened) for one week, and no difference in the HPLC-measured impurity level was noted between the two storage conditions, indicating a stability.

The invention claimed is:

1. A method for stabilizing a benzimidazole-based compound or a physiologically acceptable salt thereof, comprising incorporating by mixing together (1) a crospovidone, (2) sodium hydroxide, potassium hydroxide or a mixture thereof, and (3) a benzimidazole-based compound represented by the following Formula 1, or a physiologically acceptable salt thereof Formula 1

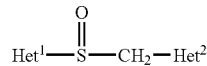

wherein $Het^1$ is

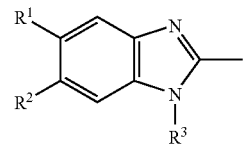

;

and $Het^2$ is

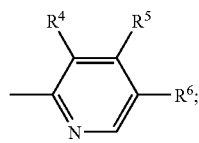

$R^1$ and $R^2$ are the same as or different from each other and are selected from hydrogen, methoxy and difluoromethoxy; $R^3$ is selected from hydrogen and sodium; and $R^4$, $R^5$ and $R^6$ are the same as or different from each other and are selected from hydrogen, methyl, methoxy, methoxypropoxy and trifluoroethoxy thereby forming a uniform mixture of components (1), (2) and (3);

wherein the benzimidazole-based compound (3) and the crospovidone (1) are incorporated with each other in a weight ratio of 0.5 to 5 part by weight to 1 part by weight of the benzimidazole-based compound and, wherein the sodium hydroxide or potassium hydroxide or their mixture (2) and the benzimidazole-based compound (3) are incorporated with each other in a weight ratio of 0.01 to 2 parts (2) to one part by weight of the benzimidazole-based compound (3) and, wherein the crospovidone (1) is present in an amount of more than 10 weight percent of the mixture.

2. A method for preventing a benzimidazole-based compound or a physiologically acceptable salt thereof from changing in color, which comprises incorporating and mixing together (1) a crospovidone, (2) sodium hydroxide, potassium hydroxide or a mixture thereof, and (3) a benzimidazole-based compound represented by the following Formula 1, or a physiologically acceptable salt thereof Formula 1

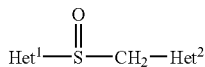

wherein $Het^1$ is

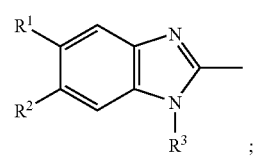

and $Het^2$ is

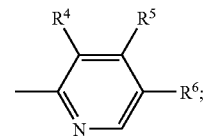

$R^1$ and $R^2$ are the same as or different from each other and are selected from hydrogen, methoxy and difluoromethoxy; $R^3$ is selected from hydrogen and sodium; and $R^4$, $R^5$ and $R^6$ are the same as or different from each other and are selected from hydrogen, methyl, methoxy, methoxypropoxy and trifluoroethoxy thereby forming a uniform mixture of components (1), (2) and (3);

wherein the benzimidazole-based compound and the crospovidone are incorporated with each other in a weight ratio of 0.5 to 5 part by weight to 1 part by weight of the benzimidazole-based compound and, wherein the sodium hydroxide or potassium hydroxide or their mixture (2) and the benzimidazole-based compound (3) are incorporated with each other in a weight ratio of 0.01 to 2 parts (2) to one part by weight of the benzimidazole-based compound (3) and, wherein the crospovidone (1) is present in an amount of more than 10 weight percent of the mixture.

* * * * *